US006647299B2

United States Patent
Bourget

(10) Patent No.: US 6,647,299 B2
(45) Date of Patent: Nov. 11, 2003

(54) PATIENT PROGRAMMER FOR IMPLANTABLE MEDICAL DEVICE WITH AUDIO LOCATOR SIGNAL

(75) Inventor: Duane L. Bourget, Albertville, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 09/960,095

(22) Filed: Sep. 21, 2001

(65) Prior Publication Data

US 2003/0060859 A1 Mar. 27, 2003

(51) Int. Cl.[7] .................................................. A61N 1/37
(52) U.S. Cl. ............................ 607/60; 607/32; 128/903
(58) Field of Search ................................. 607/2, 4, 5, 9, 607/32, 60; 128/903

(56) References Cited

U.S. PATENT DOCUMENTS 5,891,180 A * 4/1999 Greeninger et al. .......... 607/32

6,009,878 A * 1/2000 Weijand et al. ............. 128/899

OTHER PUBLICATIONS

Iaizzo et al, "System and Method for Determining Location and Tissue Contact of an Implantable Mediocal Device Within a Body", US 2002/0042632–A1, Apr. 11, 2002.*

* cited by examiner

Primary Examiner—Carl Layno
(74) Attorney, Agent, or Firm—Banner & Witcoff, Ltd.

(57) ABSTRACT

A system and method of locating the desired telemetry location for an implantable medical device includes a programmer having a patient interface to allow activation of the programmer, a bi-directional communications link between the programmer and the implantable device, an automatic gain control for determining the gain setting for a received signal from the implantable device, and an audio transducer for emitting audio signals to the patient. The bi-directional communications link enables the programmer to locate the desired telemetry location for the implantable device, the automatic gain control provides for optimum telemetry communication between the programmer and the implantable device, and the audio transducer generates audio signals indicative of the telemetry communication between the programmer and the implantable device.

47 Claims, 8 Drawing Sheets

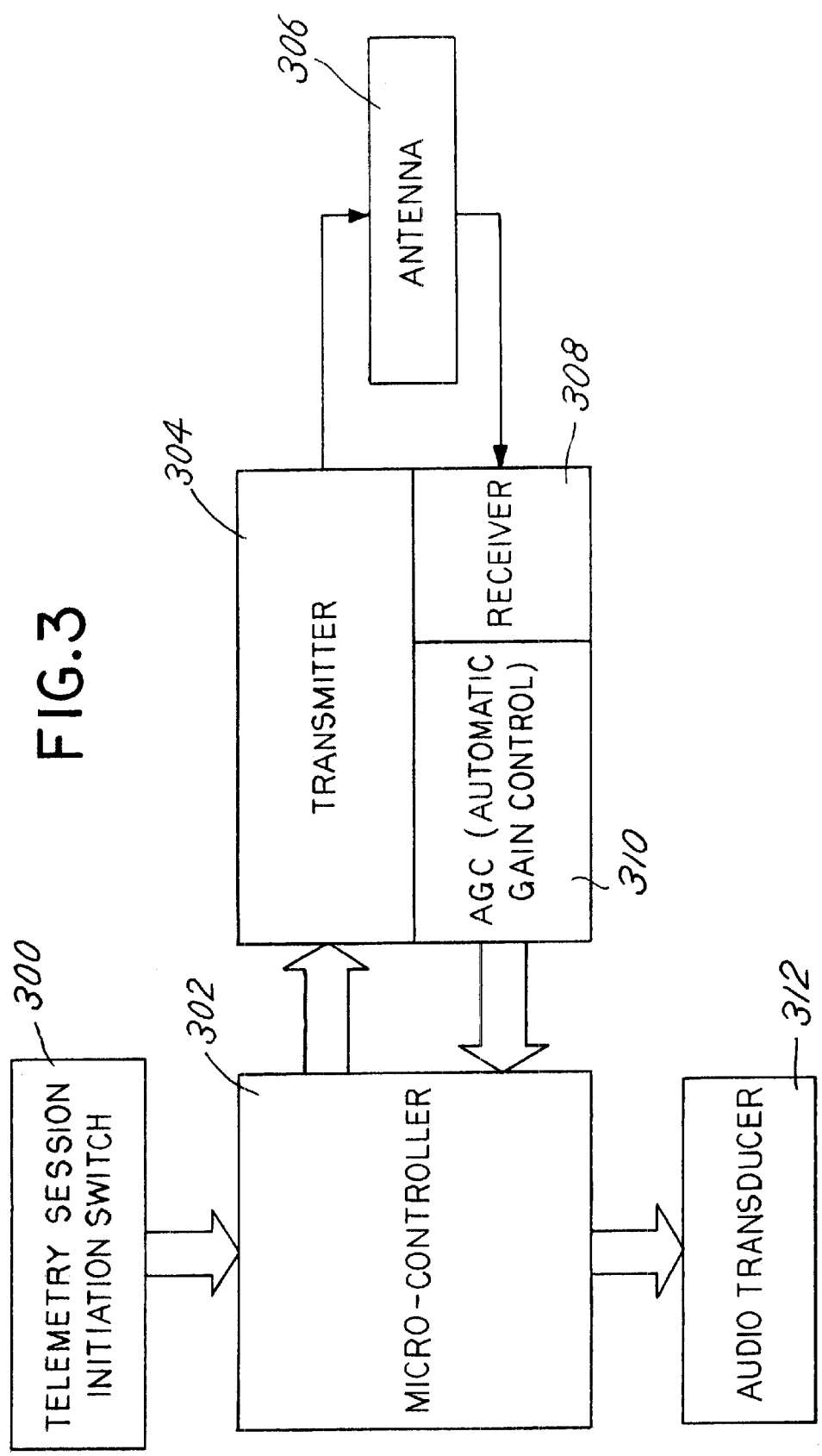

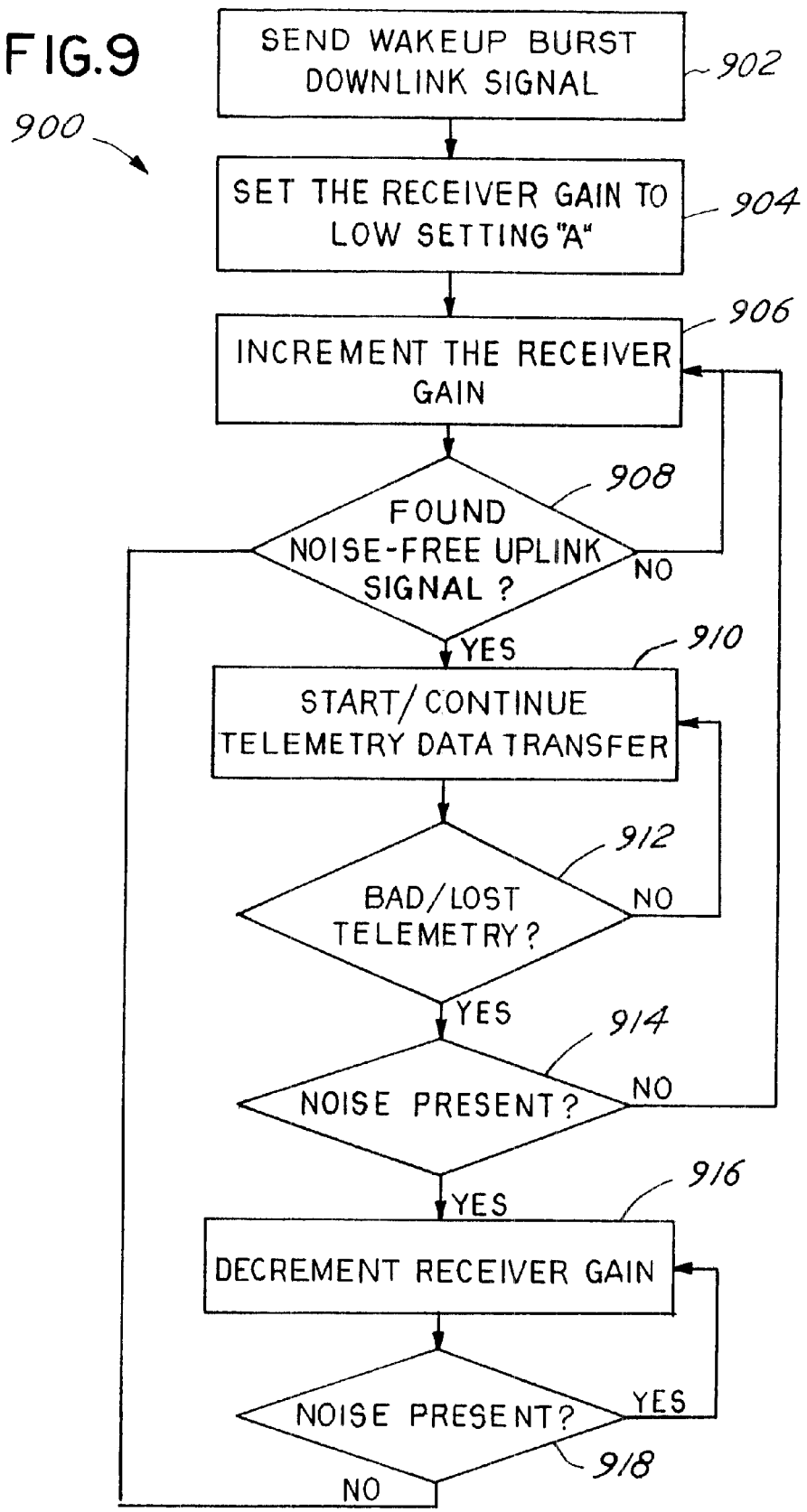

PATIENT PROGRAMMER FOR IMPLANTABLE MEDICAL DEVICE WITH AUDIO LOCATOR SIGNAL

FIELD OF THE INVENTION

This invention relates in general to systems for programming implantable medical devices, and more particularly to programmers used to program the implantable devices—programmers that use an audio locator signal to find the desired telemetry location for programming the implantable device.

BACKGROUND OF THE INVENTION

Implantable medical devices are commonly used today to treat patients suffering from various ailments, including by way of example, pain, incontinence, movement disorders such as epilepsy, Parkinson's disease, and spasticity. Additional implantable medical device therapies appear promising to treat a variety of other medical conditions, including physiological, psychological, and emotional conditions. As the number of implantable medical device therapies increases, so do the demands placed on these medical devices.

Known implantable medical devices, such as, cardiac pacemakers, tachyarrhythmia control devices, drug delivery devices, and nerve stimulators, provide treatment therapy to various portions of the body. While the present invention may be used with all implantable medical devices, by way of example and illustration, a drug delivery device will be discussed during the remainder of this section to illustrate the advantages of the invention. In the case of providing drugs to the patient, a drug delivery pump having a drug reservoir is implanted within the body. The pump is coupled to one or more catheters to deliver the drug from the reservoir to select portions of the body. The implantable drug pump provides steady, long-term delivery of drug therapy to the body and eliminates the need for frequent intravenous drug injections. Each implantable pump typically includes not only a refillable drug reservoir, but also a flow control device for regulating the drug delivery rate and, if needed, bolus injections.

Implantable drug pumps are well known in the art. Various forms of the drug pump are disclosed in U.S. Pat. Nos. 4,692,147 and 5,445,616, and are manufactured by Medtronic, Inc., Minneapolis, Minn., under the name Synchromed® drug infusion systems. The subject matter of these patents is incorporated herein by reference. Known drug delivery pumps may be either fixed rate pumps or programmable pumps. In the case of fixed-rate pumps, adjustment of the delivery rate and therefore the drug dosage may not be altered. In contrast, the drug delivery rate may be adjusted with a programmable pump through programming or reprogramming of the pump controller located within the pump. The physician may need to adjust the settings of the implanted pump for any number of reasons including, for example, to fine tune the therapy, to account for changes in the disease being treated, or to account for migration of the implanted catheter.

To achieve the programming or reprogramming of the implanted pump, a physician using an external controller, establishes a two-way telemetry communication link with the implanted pump. Once the communication link is established, through the use of radio frequency (RF) transmission, the physician may reprogram the modes of operation, parameters, and other functions of the implanted pump. In addition, the implanted pump communicates, via RF transmission, information stored in an internal memory regarding its operational status to the physician.

Specifically, a two-way telemetry link is established through the use of an RF transmitter and receiver located within the implanted pump. There is a corresponding RF transmitter and receiver in the external programmer or programming unit. Within the implanted pump, the transmitter and receiver use an antenna for receiving downlink telemetry signals and for radiating low amplitude RF signals for uplink telemetry. The telemetry transmission link used with known implanted medical pumps relies upon the generation of a low amplitude magnetic field by current oscillating in an LC circuit of an RF telemetry antenna in a transmission mode and the sensing of currents induced in a RF telemetry antenna in a receiving mode. The RF telemetry antenna of the implanted device is typically coiled wire wound around a ferrite core that is located within an airtight enclosure. The RF telemetry antenna of the programmer is contained in a programming head together with a permanent magnet which is placed over the patient's skin and over the implanted device to establish a magnetic field with the implanted device. Today, both analog and digital data can be transmitted by uplink RF telemetry from the implanted pump to the programmer.

Presently, there is a trend toward providing some degree of patient control over the reprogramming of implantable medical devices. In the case of drug delivery systems, clinical studies show that actual drug usage may be reduced if a patient believes that he or she has some degree of control over drug dosage. A terminally-ill patient who has no ability to control or self-administer a drug will frequently insist on additional dosage at each visit to a physician as a precaution against exhaustion of the drug supply before the patient's next office visit. In addition to these patient psychological aspects, there are added benefits of patient control. For example, in progressive diseases, the development of breakthrough pain may require an immediate increase in drug dosage. The ability to self-administer drug therapy may therefore reduce the number of office visits and provide immediate relief from breakthrough pain.

Before communication with, and reprogramming of, the implantable medical device can occur, the physician or patient must first locate the implantable device and then locate the desired telemetry position for programming. Presently, this is achieved by the programmer sending a wake-up pulse to the implantable device to wake up the device and begin polling the telemetry signal strength between the device and the programmer. For programming and/or monitoring of the implantable device, both uplink and downlink telemetry signal strength vary as a function programming head positioning relative to the implantable device. Therefore, it is important for the programming head to be properly positioned over the patient's implant site so that downlink RF signals can be detected in the implantable device and uplink signals can be detected by the programming head of the external programmer. For example, if the programming head is too far away from the implantable device, the attenuation of RF signals transmitted across the boundary of the patient's skin may be too great, preventing a telemetry link from being established.

Because positioning of the programmer is important for communication with the implantable device, appropriate feedback is required so that a user knows when a proper telemetry link has been established between the external programmer and the implanted device. The feedback also permits the user to position and reposition the programming head over the implant site until a suitable position is located.

In the past, various feedback techniques have been used to indicate to a user when a valid two-way telemetry link has been established. For example, programmers using a visible indicator, such as a light emitting diode (LED) or a visible alpha-numeric display, have been used to assist the physician or patient to find the desired telemetry location for the implanted device. Through variations of the visible indicator, a physician or patient will know the relative location of the programmer and the implanted device. When the programmer is in the proper telemetry position and the signal strength and accuracy are confirmed, the programmer control circuitry will cause the light indicator to indicate that a link has been established.

Programmers incorporating a visible indicator, however, suffer from many drawbacks. For instance, the visible indicator on these programmers is sometimes difficult to see depending on the orientation of the device. In addition, an implanted device is not always implanted in a location that lends itself to visual observation of the LED or visible indicator of the programmer, for example, when an implantable device is implanted in the patient's back. The visual indicator may also be difficult to see for patients with poor vision or who suffer from physical limitations, for instance, patients who cannot bend over to observe the programmer when positioned over the abdomen.

Other known programmers have utilized tactile feedback to assist the user in locating the implanted device. The programmer will vibrate when the programmer is in the desired telemetry position. These programmers, however, are ineffective for patients with spastic conditions due to tremors in their hands. This is most common with implantable drug delivery systems which are used to treat spastic conditions. In addition, if the patient is in a bumpy environment, such as a car or bus, tactile feedback would also be ineffective.

It is therefore desirable to provide a programmer that overcomes the known disadvantages with the prior art and locates the desired telemetry location for an implantable medical device.

BRIEF SUMMARY OF THE INVENTION

In an exemplary embodiment, the present invention provides for the use of audio feedback in conjunction with the positioning of the programmer for performing telemetry between the implantable device and the programmer. Audio feedback allows a user to locate an implantable device with a hand-held programmer without looking for an indicator light or alpha-numeric display, or without trying to sense a vibration in the programmer. In one embodiment, the programmer resonates audio tones that may vary in frequency depending on the relative position of the programmer and the implanted device. Once the desired telemetry location is located, the programmer notifies the patient to that effect through the use of another audio indicator.

The full range of objects, aspects and advantages of the invention will become apparent and appreciated by referring to the following detailed description and claims taken in conjunction with the accompanying drawings.

BRIEF DESCRIPTION OF THE DRAWINGS

FIG. 3 is a general depiction of the components of the programmer of the present invention.

FIG. 9 shows a detailed flowchart of an exemplary gain control algorithm for an implantable pump.

DETAILED DESCRIPTION OF THE INVENTION

Figure 2:
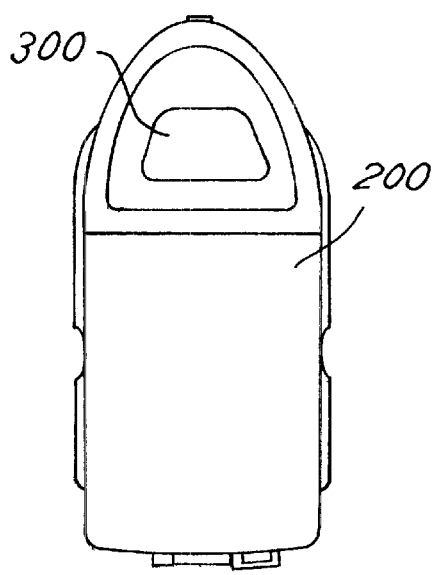
FIG. 2 shows an exemplary embodiment of an external hand-held programmer of the present invention for communication with the implantable medical device of FIG. 1.
Figure 1:
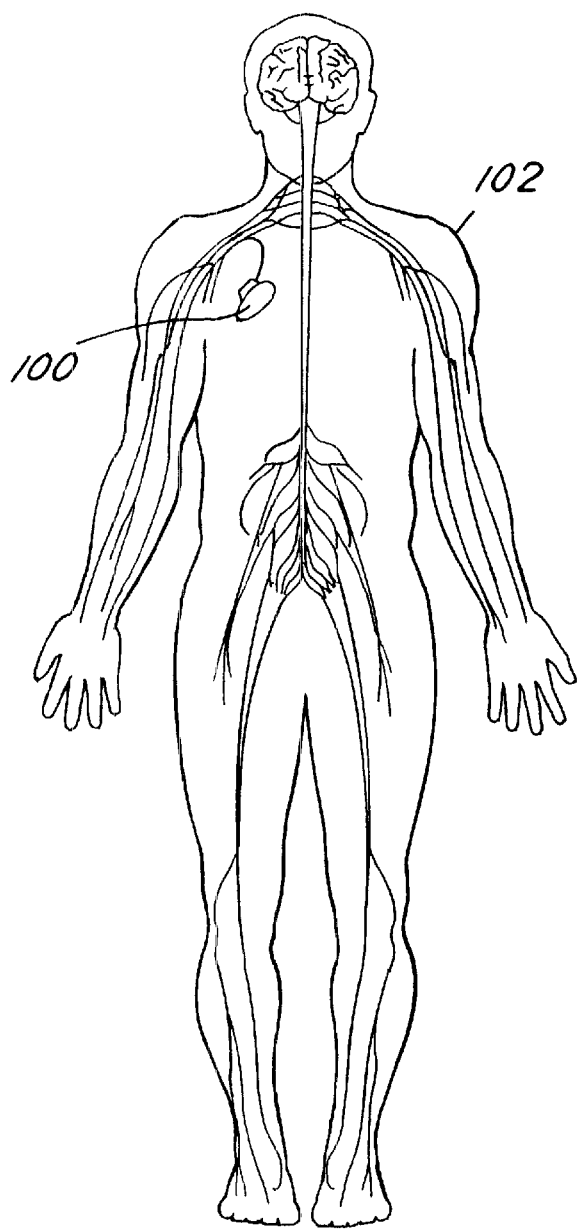
FIG. 1 shows an implantable medical device in a body.

Referring to FIGS. 1 and 2, an exemplary embodiment of a hand-held programmer 200 is depicted and is used to locate a medical device 100 implanted in body 102. The programmer 200 establishes a bi-directional communication link with the implantable medical device, such as a drug infusion system. Those of skill in the art will understand that the present invention may be used with other implantable medical devices including, by way of example, cardiac pacemakers, neurostimulators, muscle stimulators, brain stimulators, cardioverter/defibrillator, monitoring devices, or any other implantable device that would benefit from telemetry capabilities according to the present invention.

The programmer 200 is preferably a hand-held unit adapted to be placed in close proximity to the patient's body over the implant site of the patient's implanted medical device to establish the communication link. Once the programmer is in position and a telemetry link has been established, the programmer may then be used to program or reprogram the implanted device, in any manner known to those skilled in the art. As discussed in more detail below, the programmer 200 includes several components, including a patient interface or telemetry initiation switch 300, a programmer head, a battery, a transmitter, a receiver, an antenna, a micro-controller, and an audio feedback to provide the user with information as to the proper positioning of the programmer 200 relative to the implantable medical device 100. As used herein, audio feedback refers to any feedback perceivable by a user's sense of sound, e.g., audible tones emanating from the programmer 200, voice recordings, etc.

As stated above, the implantable medical device 100 used with the present invention may be any type of implantable device that provides treatment to the patient. As such, the medical device 100 will be generally described to include a hermetically sealed housing containing components, such as, control circuitry, monitoring circuitry, battery, and transmitter and receiver circuitry coupled to an antenna. As understood by those skilled in the art, the transmitter/receiver circuitry generates modulated radio frequency (RF) signals, which are provided to the antenna such that electromagnetic waves are radiated by the antenna and ultimately detected and demodulated by the programmer 200.

FIG. 3 illustrates generally a diagram of constituent components of one embodiment of the programmer 200. As illustrated, the programmer 200 includes a telemetry session initiation switch 300, micro-controller 302, transmitter 304, antenna 306, receiver 308, automatic gain control 310, and an audio transducer 312. The telemetry session initiation switch 300 may be a button or switch for activating the programmer, and more particularly, for activating the micro-controller 302. The micro-controller 302 is the component that controls the audio transducer 312, which provides audio signals indicative of the relative location of the programmer and implantable device. The micro-controller 302 also initiates the transmitter 304, which sends a signal, or wake-up burst, via the antenna 306 to the implantable device 100. In particular, the transmitter 304 generates modulated RF signals for provision to antenna 306 such that electromagnetic waves are radiated. These electromagnetic waves are received by the antenna and transmitter/receiver circuitry of the implanted medical device and demodulated. Upon sending the wake-up burst, the micro-controller 302 activates the receiver 308 for receiving a return feedback RF signal from the implanted device. The feedback signal, which is also an electromagnetic wave radiated by the implanted device, is received by the antenna 306 and then sent to the receiver 308 where it is demodulated and sent to the micro-controller 302 for processing.

An automatic gain control 310 may be used with the invention to adjust the amplitude of the feedback signal from the implantable device. It should be understood that the automatic gain control 310 may be hardware circuitry within the programmer or software run by the micro-controller 302. Nevertheless, it is preferred that with either the hardware or software automatic gain control, the gain should be set to receive the maximum signal from the implantable device without excessive background noise. In other words, the receiver gain is adjusted depending on the signal to noise ratio of the feedback signal from the implantable device. The automatic gain control may be used to determine signal strength by comparing the amplitude or width of the feedback signal against a referenced amplitude or width programmed into the programmer.

Figure 7:
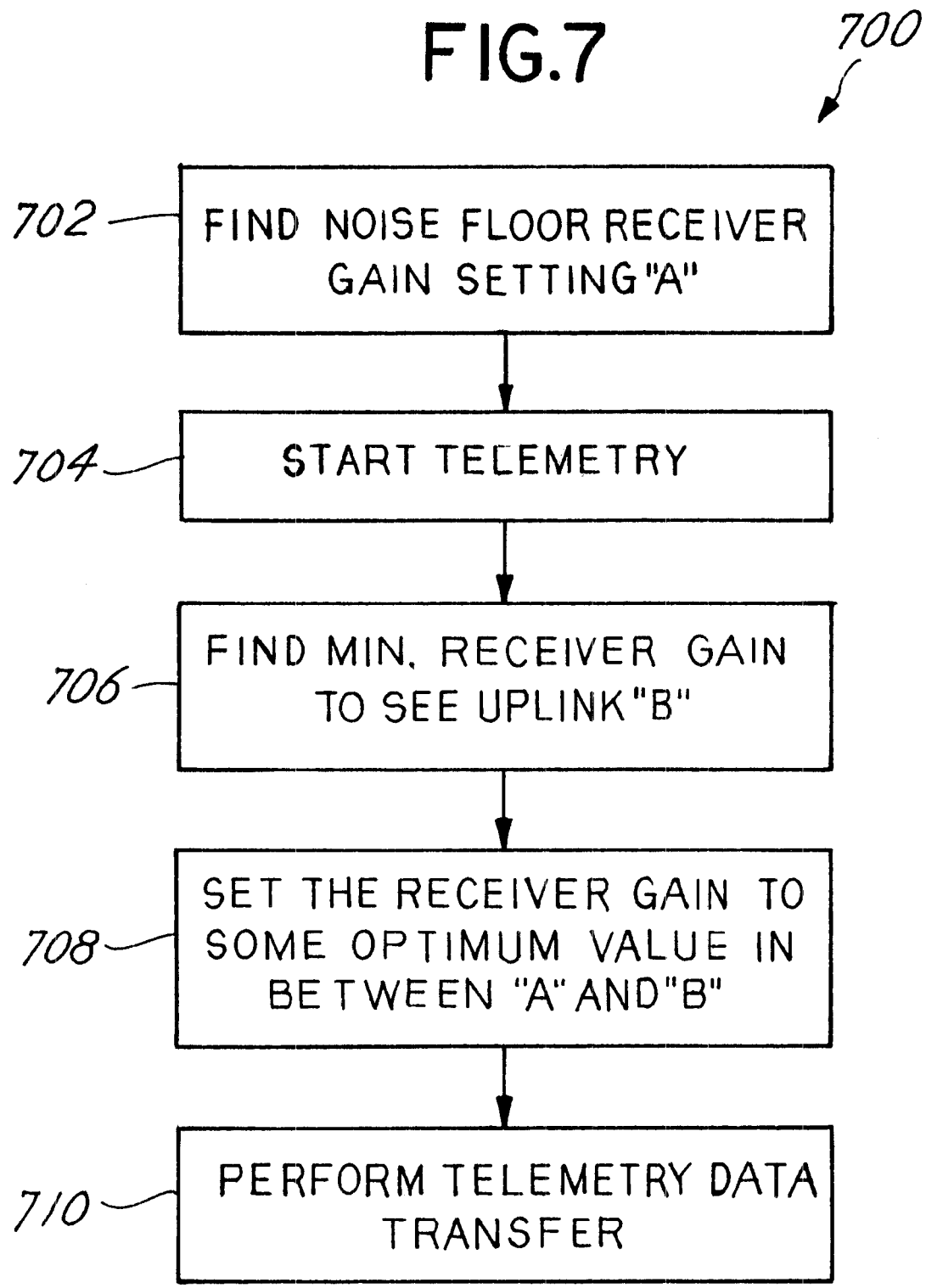
FIG. 7 shows a general flowchart of an exemplary gain control algorithm.

Referring to FIG. 7, there is illustrated a general flow diagram of an exemplary gain control algorithm programmed into the gain control 310, or software controlled by the micro-controller 302, to provide the desired gain setting for the receiver 308. The depicted algorithm 700 begins at step 702 where the automatic gain control 310 determines the noise floor gain setting "A". At step 704, the telemetry session is initiated and the feedback signal is received from the implanted device. As discussed below, the audio transducer 312 of the programmer will simultaneously provide audio feedback to the user indicating that the search is under way for the signal. The automatic gain control 310 then, at step 706, finds the minimum receiver gain to detect the uplink signal "B" from the implanted device. At step 708, the automatic gain control sets the receiver gain to an optimum value in between the setting "A" and uplink "B". Once the receiver gain is set, at step 710 the audio transducer will provide audio signals to this effect and the programmer may begin to perform the transfer of telemetry data from the implanted device until the transfer is complete.

Figure 8:
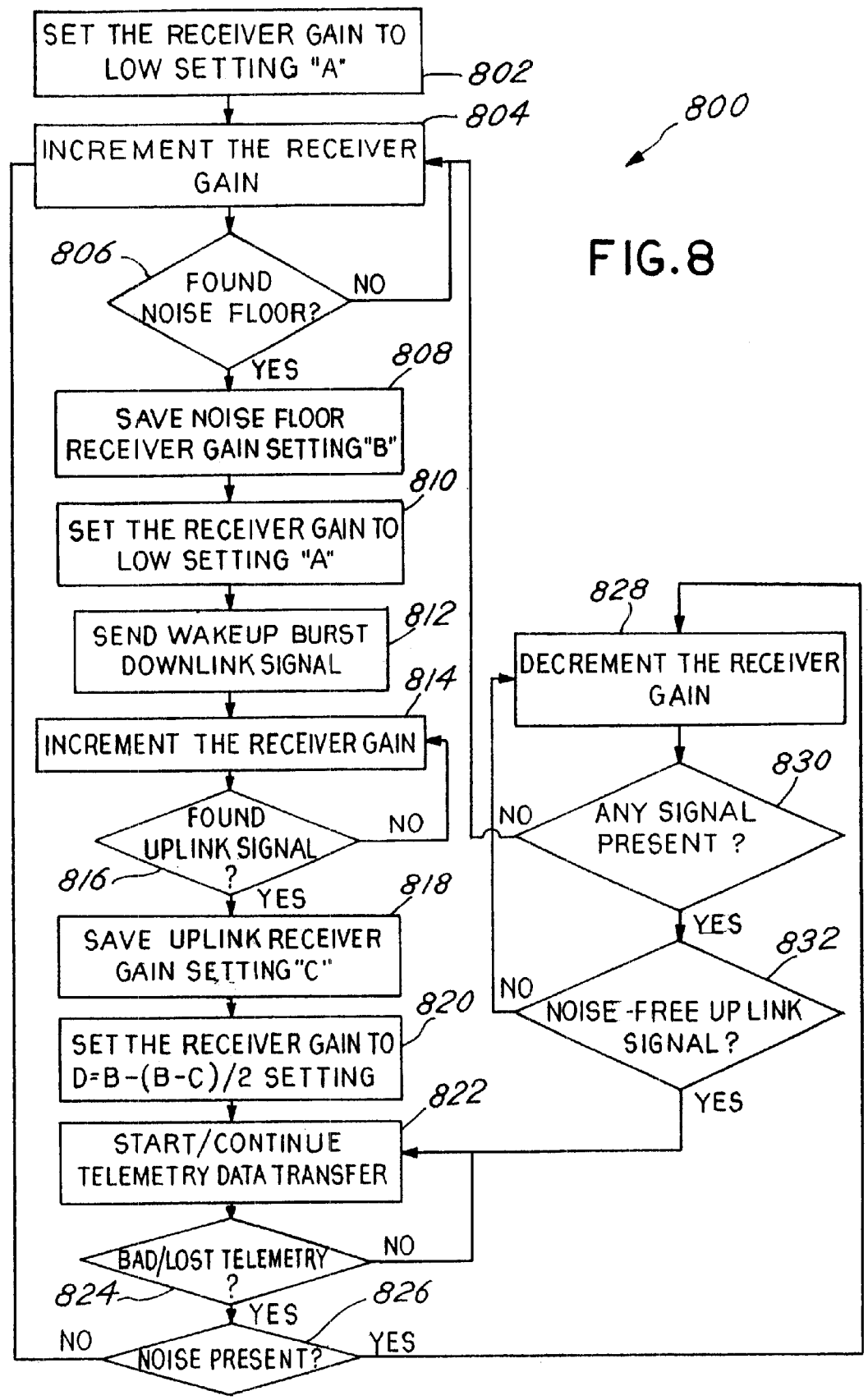
FIG. 8 shows a more detailed flowchart of an exemplary gain control algorithm.

Referring to FIG. 8, there is illustrated a more detailed flow diagram of an exemplary gain control algorithm. As above, the exemplary gain control algorithm is programmed into the gain control 310, or is software controlled by the micro-controller 302, to provide the desired gain setting for the receiver 308. The depicted algorithm 800 begins at step 802 where the automatic gain control 310 sets the receiver gain to a low setting "A". The automatic gain control 310 then increments the receiver gain, at step 804, and determines whether the noise floor is found, step 806. That is, the automatic gain control determines the minimum receiver gain needed to overcome the noise present in the signal. If the noise floor is not found, the automatic gain control 310 continues to increment the receiver gain. Audio signals may be provided by the audio transducer 312 indicating that the programmer is searching for the noise floor. Once the floor noise is found, at step 808, the automatic gain control 310 saves the floor noise receiver gain setting "B". At step 810, the automatic gain control 310 again sets the receiver gain to a low setting "A". The programmer then sends a wake up burst downlink signal to the implanted device, at step 812. The automatic gain control 310 again increments the receiver gain, at step 814, and determines whether the programmer has found an uplink signal from the implanted device, step 816. If not, the automatic gain control 310 continues to increment the receiver gain. Audio signals may again be provided by the audio transducer indicating that the automatic gain control is adjusting the receiver gain. Once the uplink signal is found, at step 818 the automatic gain control 310 saves the uplink receiver gain setting "C". At step 820, the automatic gain control 310 performs the following calculation to set the receiver gain setting: D=B−(B−C)/2. Once receiver gain setting "D" is set, at step 822, the audio transducer may provide audio signals to this effect and the telemetry data transfer may begin and will continue until the transfer is complete or the telemetry signal becomes poor or is lost, step 824. If the signal is poor or lost, the automatic gain control 310, at step 826, determines whether the poor or lost telemetry signal is a result of noise being present. If no noise is present, the automatic gain control 310 will increment the receiver gain, step 804, and will repeat the algorithm described above. If noise is present, the automatic gain control 310 will decrease the receiver gain at step 828 and then determine whether a signal is present, step 830. If no signal is present, the automatic gain control 310 will increment the receiver gain, step 804, and will repeat the algorithm described above. If a signal is present, the automatic gain control 310 will determine at step 832 whether the signal is a noise free uplink signal. If it is, the telemetry data transfer will start, or continue if previously started, step 822. If the uplink signal is not noise free, the automatic gain control 310 will again decrease the receiver gain, step 828, until a noise free uplink signal is present. The telemetry data transfer may then start or continue, if previously started, until the data transfer is complete. It should be understood that audio signals may be provided during any stage of the aforementioned algorithm, including, but not limited to, when the automatic gain control is adjusting the receiver gain or determining whether noise is present in the signal.

Referring to FIG. 9, there is illustrated a more detailed flow diagram of an exemplary gain control algorithm for a drug pump or similar drug delivery device. As above, audio signals may be provided at any stage of this gain control algorithm to provide feedback to the user of the programmer of the telemetry status. The depicted algorithm 900 begins at step 902 where the programmer sends a wake up burst signal to the implanted device. The automatic gain control 310, at step 904, sets the receiver gain to low setting "A". The automatic gain control 310 increments the receiver gain, at step 906, and determines whether a noise free signal is present, step 908. If a noise free signal is not present, the automatic gain control 310 will continue to increment the receiver gain. Again, audio signals may be provided to indicate that noise is still present in the signal. Once a noise free signal is found, at step 910 the telemetry data transfer from the implanted device to the programmer may begin and will continue until the transfer is complete or the telemetry signal becomes poor or is lost, step 912. If the signal is poor or lost, the automatic gain control 310, at step 914, determines whether the poor or lost telemetry signal is a result of noise being present. If no noise is present, the automatic gain control 310 will increment the receiver gain, step 906, and will repeat the algorithm described above. If noise is present, the automatic gain control 310 will decrease the receiver gain at step 916 and then determine whether a noise free signal is present, step 918. If noise is still present, the automatic gain control will continue to decrease the receiver gain until a noise free signal remains. If no noise is present, the programmer will start or continue, if previously started, the telemetry data transfer, steps 908, 910, until the data transfer is complete.

Figure 4:
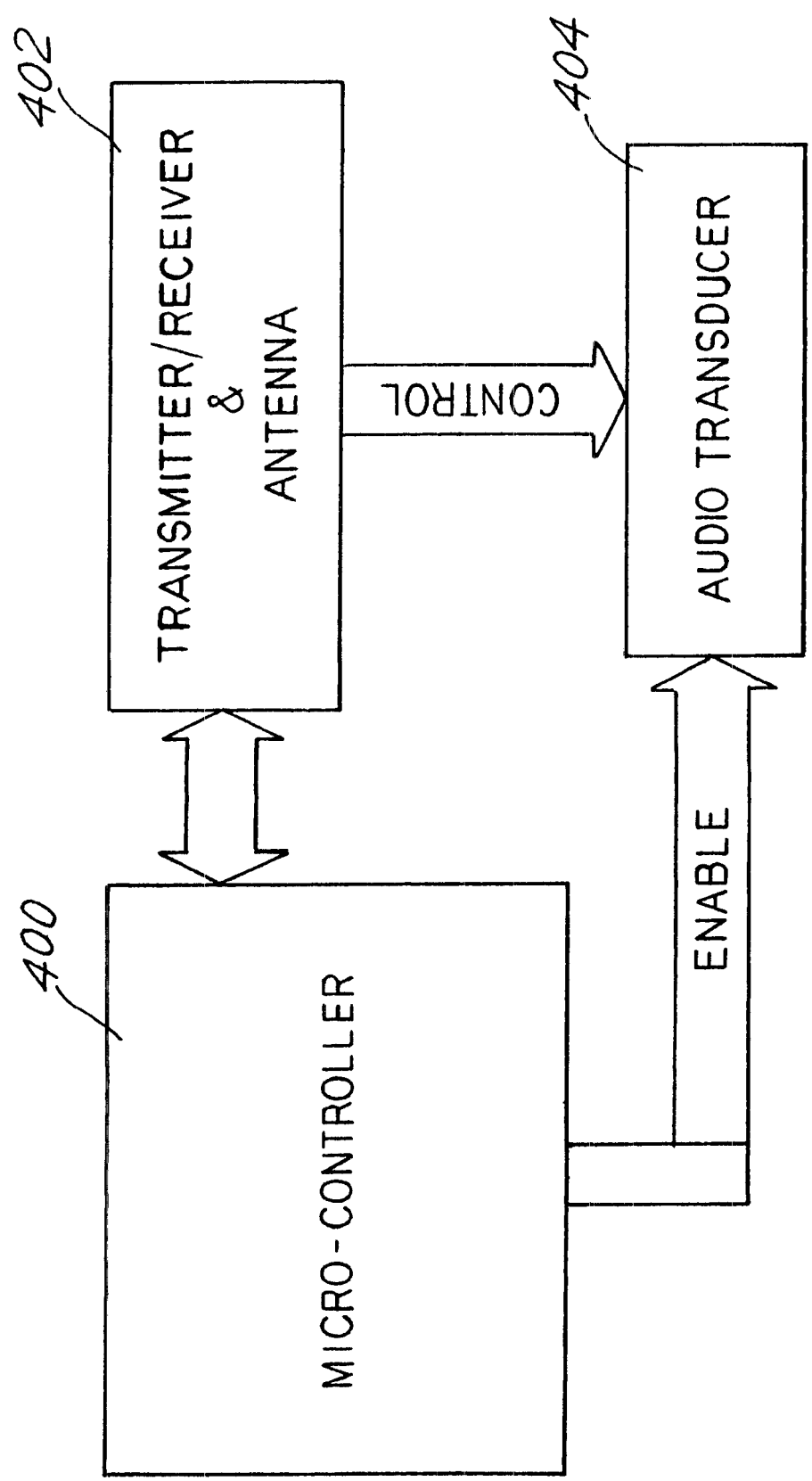
FIG. 4 is general depiction of an alternative embodiment of the components of the programmer of the present invention.

Referring to FIG. 4, there is illustrated an alternative embodiment of constituent components of the programmer 200. In this embodiment, the programmer 200 includes a micro-controller 400 that controls the functions of the transmitter/receiver and antenna 402. As depicted, the micro-controller further enables the audio transducer 404. With this embodiment, the transmitter/receiver 402 control the audio transducer, which produces audio signals indicative of the relative location of the programmer and implanted device In an effort to conserve the programmer's battery power, software may be implemented with the invention to permit the programmer to search for the implantable device using a lower field strength. If the programmer is unable to locate the implantable device using the lower field strength, the programmer may increase the amplitude in an effort to locate the implanted device. This software control results is less current being drawn from the battery by the programmer during operation.

As would be known to those skilled in the art, the programmer transmitter and the implantable device receiver include circuitry that is compatible and operable for receiving and demodulating the transmitted signal from the programmer to the implanted device. Likewise, the programmer receiver and implantable device transmitter include circuitry that is compatible and operable for receiving and demodulating the transmitted signal therebetween.

The antenna 306 is preferably disposed within the programmer 200. Because of this antenna location, the programmer can be conveniently placed in proximity to the patient's implant site. When so positioned, antenna 306 receives uplink telemetry signals transmitted from the implanted device and transmits downlink telemetry signals to be received by the implanted device. A bi-directional communication link is then established between the programmer and the implanted device.

To provide feedback as to the proper positioning of the programmer relative to the implanted medical device to establish a valid communication link, an audio feedback device is used. As preferred and depicted, the audio feedback device is provided as an audio transducer 312 that transmits an audio indicator tone to the patient or user of the programmer. While many possible audio indicator tones may be used, it is preferred that the audio indicator tone vary depending on the relative telemetry signal strength between the programmer and the implanted device. Unlike conventional indicator devices, audio feedback generation allows a user to locate the implanted device without the requirement of looking at an indicator light or sensing a vibration in the programmer. While the present invention replaces the conventional indicators, it should be understood by those skilled in the art that audio indication may be used in conjunction with light indicators or tactile feedback devices.

Figure 5:
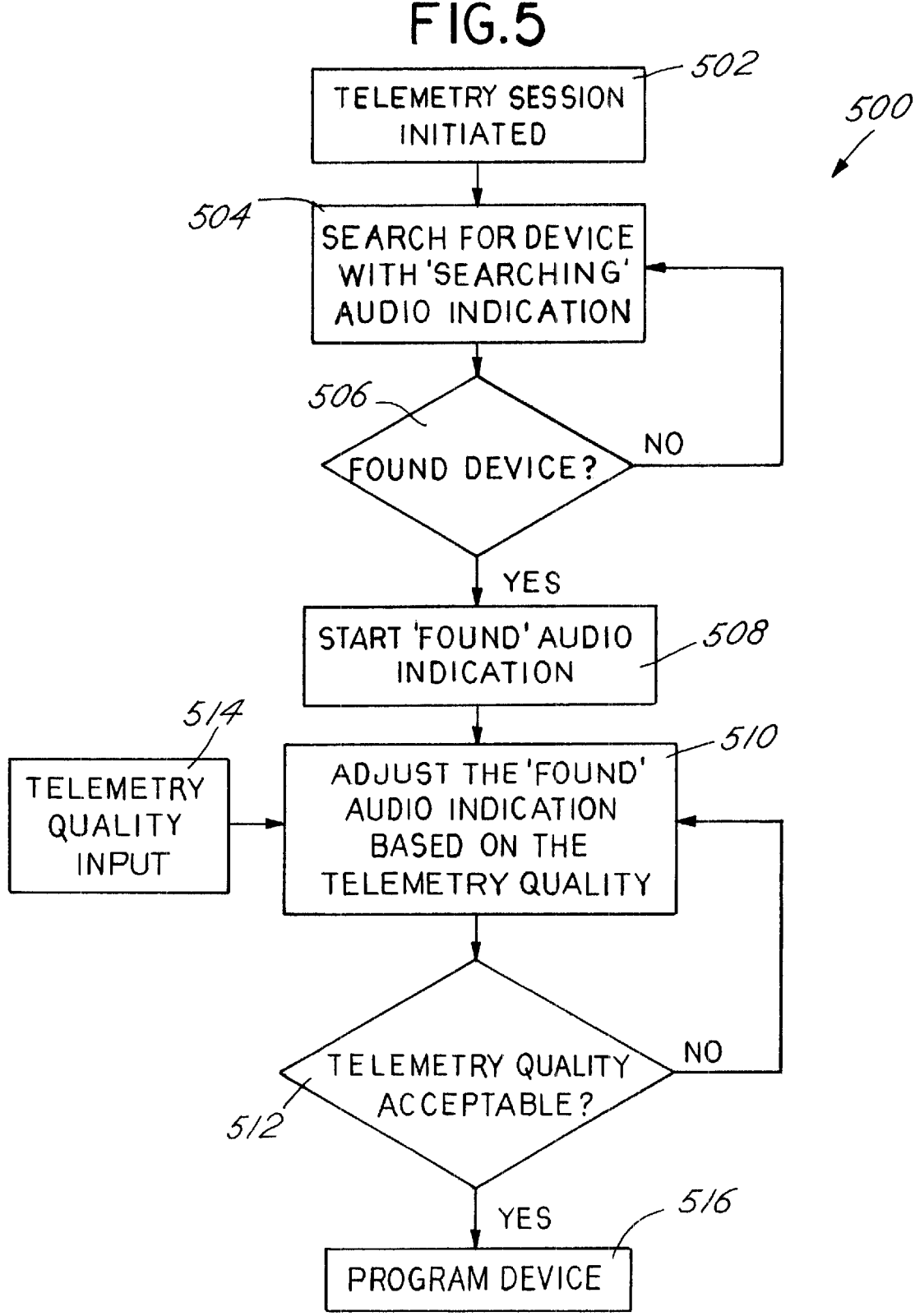
FIG. 5 shows a flowchart of an illustrative telemetry session of the present invention.

The use of audio feedback in positioning the programmer for performing telemetry according to the present invention is generally described with reference to the method 500 of FIG. 5. Programmer positioning method 500 generally includes the initiation of a telemetry session as shown in step 502. For example, a telemetry session may be initiated by the programmer sending a wake-up burst to the implanted device. Thereafter, at step 504, the programmer will begin to look for the implanted device. The audio transducer of the programmer will simultaneously provide audio feedback to the user indicating that the search is under way.

At step 506, if the programmer does not find the implanted device, the programmer will keep searching until it is located by employing the exemplary gain control algorithm described above. Once the implanted device is located, at step 508, the programmer may provide a "found" audio indication. The "found" indication may be any desired audio indicator, including by way of example, a constant tone, a rapid repeating tone, or silence. Programmer telemetry is then attempted to determine whether valid telemetry has been accomplished or, in other words, whether a valid communication link is established between the implanted device and the programmer. As described above with respect to the gain control algorithms, if a valid telemetry link is not established, at step 510, the audio transducer of the programmer will provide audio feedback to the user to that effect. The user will then know that the programmer must be moved relative to the implanted device. As the user moves the programmer, the "found" audio indicator will vary based on the telemetry quality determined by the automatic gain control. If the telemetry quality is poor, at step 512, the programmer will provide an audio indicator to that effect to the user. By way of example and not limitation, the audio signal may be a lower frequency signal as the programmer is far away from the implanted device. As the programmer moves closer to the implanted device to the desired telemetry location, the frequency of the signal may increase. As illustrated by step 514, input parameters may be provided to the programmer to set the minimum telemetry quality for programming the implanted device. For example, the telemetry quality input parameters may be determined by the ratio of the signal width or signal amplitude over the background noise.

Once the telemetry quality is acceptable and the programmer is in proper telemetry position, the programmer will provide an audio signal indicating that a proper communication link has been established. Once in proper position, at step 516, the programmer will program the implanted device with the desired parameters set by the physician or the patient.

As shown by the above programmer positioning method, the audio feedback of the present invention creates a 'closed loop' system. That is, the programmer uses quality of the communication link with the implanted device to provide feedback to the patient who then updates the location of the programmer accordingly to improve the quality of the communication link with the implanted device.

One skilled in the art will readily recognize that various techniques may be used for determining valid telemetry. For instance, valid uplink telemetry may be determined, valid downlink telemetry may be determined, bi-directional valid telemetry may be determined, signal strength may be used for determining valid telemetry, or any other processes or combination of processes for determining that a link is valid may be used according to the present invention.

Further, one skilled in the art will recognize that audio feedback may be used in different manners to indicate valid telemetry under different circumstances or different applications. For example, audio feedback may be used upon initial detection of a valid communication link even though the programmer may not be at a position that provides a signal of optimum strength. Audio feedback may also be used only upon finding a communication position that provides a telemetry signal of a particular strength as determined by a predetermined reference strength level. Further, audio feedback may be used to indicate an initial detection of a valid communication link with the audio signal being modified as a function of signal strength as positions providing greater or lesser signal strength are located. Still other manners of indicating valid telemetry are possible and are considered to be within the scope of the present invention.

Figure 6:
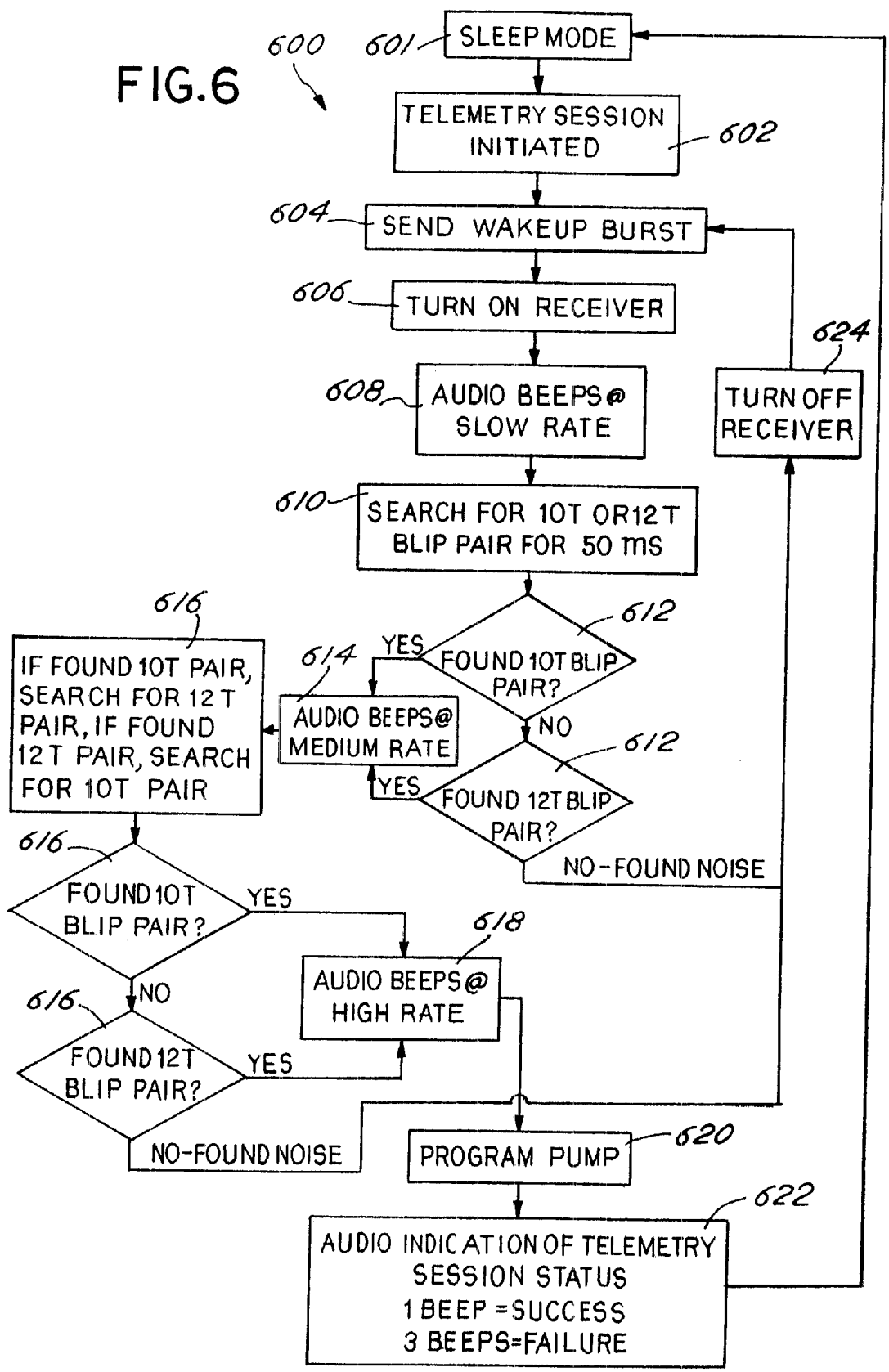
FIG. 6 shows a more detailed flowchart of an illustrative telemetry session of the present invention.

Referring to FIG. 6, a more detailed alternative method 600 of locating an implantable device through the use of audio feedback is depicted. Programmer positioning method 600 generally begins with the programmer in sleep mode 601 and includes the initiation of a telemetry session as shown in step 602 by the user activating the programmer. The programmer sends a wake-up burst to the implanted device, step 604, and activates the receiver within the programmer, step 606. The programmer then begins to locate the implanted device. At step 608, the programmer initially begins providing an audio indicator in the form of an audio beep. In an exemplary embodiment, the audio indicator begins to beep at a slow rate. At step 610, the programmer searches for the implanted device by looking for blip pairs, or signals having a predetermined spacing, transmitting from the implanted pump. In one embodiment of the invention, at step 612, the programmer will look for either a 10T blip pair having, for example, a signal spacing of 600 microseconds, or a 12T blip pair having, for example, a signal spacing of 720 microseconds. Once either blip pair is located, at step 614, the programmer will adjust the rate of the audio beep. At step 616, the programmer will look for the other blip pair. If this second blip pair is found, at step 618, the programmer will again adjust the rate of the audio beep. Upon locating each of the blip pairs, at step 620, the programmer programs the implanted device and, at step 622, will indicate whether the telemetry session was successful. If the blip pairs are not found, at step 624, the programmer will turn off the receiver and resend a wake-up burst or beacon to the implanted device, step 604. The programmer will then restart the process of locating the implanted device and the desired telemetry position.

Those skilled in the art recognize that the preferred embodiments, including the methods of locating the desired telemetry location for the programmer described herein, may be altered and modified without departing from the true spirit and scope of the invention as defined in the appended claims.

What is claimed is:

1. A patient programmer for locating an implantable medical device and determining telemetry quality between the programmer and implantable medical device comprising:
   a patient interface to allow activation of the programmer,
   a transmitter for sending a first signal to the implantable medical device,
   a receiver for receiving a second signal from the implantable medical device,
   an automatic gain control for determining telemetry signal quality between the programmer and the implantable medical device, and
   an audio transducer for generating audio signals indicative of the telemetry signal quality determined by the automatic gain control.

2. The patient programmer of claim 1 wherein the automatic gain control is implemented through software.

3. The patient programmer of claim 1 further comprising a micro-controller for initiating the transmitter and an antenna for transmitting the first signal to the implantable medical device and for receiving the second signal from the implantable medical device.

4. The patient programmer of claim 3 wherein the automatic gain control adjusts the strength of the second signal received from the implantable medical device.

5. The patient programmer of claim 1 wherein the patient interface is a telemetry initiation switch.

6. The patient programmer of claim 1 wherein the audio transducer provides audio signals of varying frequency based on the telemetry quality signal determined by the automatic gain control.

7. The patient programmer of claim 1 wherein the implantable medical device includes an implantable device selected from the group consisting of a cardiac pacemaker, a neurostimulator, a muscle stimulator, a brain stimulator, a cardioverter/defibrillator, a monitoring device, and a drug pump.

8. The patient programmer of claim 1 wherein the automatic gain control determines a minimum gain for the receiver to overcome noise present in the second signal.

9. The patient programmer of claim 1 wherein the automatic gain control determines a signal to noise ratio of the second signal, and wherein a gain for the receiver is adjusted by the automatic gain control based on the signal to noise ratio of the second signal.

10. The patient programmer of claim 9 wherein the audio transducer provides audio signals of varying frequency based on the gain adjustments made by the automatic gain control.

11. A system of locating the desired telemetry location for an implantable medical device comprising:
    a programmer having a patient interface to allow activation of the programmer and entry of therapy parameters by a patient,
    a bi-directional communications link between the programmer and the implantable medical device to enable the programmer to locate the desired telemetry location for the implantable medical device and to enable the programmer to program the implantable medical device,
    an automatic gain control for determining telemetry signal quality between the programmer and the implantable medical device, and
    an audio transducer for generating audio signals indicative of the telemetry signal quality determined by the automatic gain control.

12. The system of claim 11 wherein the programmer includes a transmitter and antenna for sending a first signal to the implantable medical device.

13. The system of claim 11 wherein the programmer includes a receiver for receiving a second signal from the implantable medical device.

14. The system of claim 13 wherein the automatic gain control adjusts the strength of the second signal based on the quality of the telemetry signal.

15. The system of claim 14 wherein the audio transducer provides audio signals of varying frequency based on the adjustment of the strength of the second signal by the automatic gain control.

16. The system of claim 11 wherein the implantable medical device includes an implantable device selected from the group consisting of a cardiac pacemaker, a neurostimulator, a muscle stimulator, a brain stimulator, a cardioverter/defibrillator, a monitoring device, and a drug pump.

17. The system of claim 12 wherein the programmer includes a micro-controller for initiating the transmitter.

18. The system of claim 11 wherein the patient interface is a telemetry initiation switch.

19. The patient programmer of claim 13 wherein the automatic gain control determines a minimum gain for the receiver to overcome noise present in the second signal.

20. The patient programmer of claim 19 wherein the automatic gain control determines a signal to noise ratio of the second signal, and wherein a gain for the receiver is adjusted by the automatic gain control based on a signal to noise ratio of the second signal.

21. The patient programmer of claim 20 wherein the audio transducer provides audio signals of varying frequency based on the gain adjustments made by the automatic gain control.

22. The patient programmer of claim 11 wherein the automatic gain control is implemented through software.

23. An external device for locating an implantable medical device comprising:

a programmer having an initiation switch, a transmitter, a receiver, an audio transducer, and an automatic gain control, the transmitter sending a first signal to the implantable medical device, the receiver receiving a second signal from the implantable medical device, the automatic gain control adjusting the strength of the second signal based on the quality of the second signal, and the audio transducer generating an audio signal indicative of the strength of the second signal as determined by the automatic gain control.

24. The external device of claim 23 wherein the automatic gain control determines a signal to noise ratio of the second signal.

25. The external device of claim 24 wherein a gain for the receiver is adjusted by the automatic gain control based on the signal to noise ratio of the second signal.

26. The external device of claim 25 wherein the audio signal varies in frequency based on the gain adjustments made by the automatic gain control.

27. The external device of claim 23 wherein the automatic gain control is implemented through software.

28. The external device of claim 23 wherein the implantable medical device includes an implantable device selected from the group consisting of a cardiac pacemaker, a neurostimulator, a muscle stimulator, a brain stimulator, a cardioverter/defibrillator, a monitoring device, and a drug pump.

29. The external device of claim 23 wherein the programmer includes an antenna for receiving the second signal.

30. A method of finding a desired telemetry location for an implantable medical device comprising the steps of:

providing a programmer having a transmitter, a receiver, a micro-controller, an automatic gain control, and an audio transducer, establishing a bi-directional communications link between the programmer and the implantable medical device, determining the desired telemetry quality of the bi-directional communications link, and transmitting an audio signal indicative of the telemetry quality between the programmer and the implantable medical device.

31. The method of claim 30 further comprising the step of programming the implantable medical device using the programmer.

32. The method of claim 31 wherein the step of programming the implantable medical device is performed via telemetry.

33. The method of claim 32 further comprising the step of locating a first signal from the implantable medical device.

34. The method of claim 33 further comprising the step of determining a signal strength of the first signal.

35. The method of claim 34 further comprising the step of transmitting a plurality of audio signals of varying frequencies indicative of the strength of the first signal.

36. The method of claim 33 wherein the step of determining the desired telemetry quality includes the step of determining the telemetry quality of the first signal from the implantable device.

37. The method of claim 33 wherein the step of determining the desired telemetry quality includes the step of determining a signal to noise ratio of the first signal from the implantable device.

38. The method of claim 33 wherein the step of determining the desired telemetry quality includes the step of setting a receiver gain.

39. The method of claim 38 wherein the step of determining the desired telemetry quality includes the step of incrementing the receiver gain until the desired telemetry quality is located.

40. The method of claim 39 wherein the step of determining the desired telemetry quality includes the step of providing audio signals indicative of the incrementation of the receiver gain.

41. A method of finding the desired telemetry location for an implantable medical device comprising the steps of:

providing a programmer having a transmitter, a receiver, an automatic gain control, and an audio transducer, transmitting a first signal from the transmitter to the implantable medical device, receiving a second signal from the implantable medical device by the receiver, determining a receiver gain by the automatic gain control based on the telemetry quality of the second signal, and transmitting an audio signal from the audio transducer to a patient indicative of the telemetry quality of the second signal.

42. The method of claim 41 further comprising the step of programming the implantable medical device using the programmer.

43. The method of claim 41 wherein the step of programming the implantable medical device is performed via telemetry.

44. The method of claim 41 further comprising the step of transmitting a plurality of audio signals of varying frequencies indicative of the telemetry quality of the second signal.

45. The method of claim 41 wherein the step of determining the receiver gain includes the step of determining a signal to noise ratio of the second signal from the implantable device.

46. The method of claim 41 wherein the step of determining the receiver gain includes the step of incrementing the receiver gain until the desired telemetry quality is located.

47. The method of claim 46 further comprising the step of providing audio signals indicative of the incrementation of the receiver gain.

* * * * *